United States Patent [19]

Knifton

[11] 4,356,327
[45] Oct. 26, 1982

[54] PROCESS FOR PREPARING PROPYLENE GLYCOL MONOALKYL ETHERS AND ALKOXYACETONES

[75] Inventor: John F. Knifton, Austin, Tex.

[73] Assignee: Texaco Inc., White Plains, N.Y.

[21] Appl. No.: 316,193

[22] Filed: Oct. 29, 1981

[51] Int. Cl.³ .................... C07C 45/49; C07C 41/01
[52] U.S. Cl. .................................... 568/387; 568/678
[58] Field of Search .................. 568/387, 852, 678

[56] References Cited

U.S. PATENT DOCUMENTS

| | | | |
|---|---|---|---|
| 2,830,089 | 4/1958 | Fitzwilliam et al. | 568/387 |
| 2,876,254 | 3/1959 | Jenner et al. | 568/387 |
| 3,857,893 | 12/1974 | Nozaki | 568/387 |
| 4,071,568 | 1/1978 | Onoda et al. | 568/678 |
| 4,079,085 | 3/1978 | Wall | 568/678 |
| 4,200,765 | 4/1980 | Goetz | 568/852 |
| 4,308,403 | 12/1981 | Knifton | 568/678 |
| 4,317,943 | 3/1982 | Knifton | 568/678 |

*Primary Examiner*—Natalie Trousof
*Assistant Examiner*—James H. Reamer
*Attorney, Agent, or Firm*—Carl G. Ries; Walter D. Hunter; Jack H. Park

[57] ABSTRACT

Propylene glycol monoalkyl ethers and alkoxyacetones are formed by contacting a mixture of carbon monoxide and hydrogen and (a) acetaldehyde or (b) an acetal and an alcohol, with a catalyst comprising a cobalt-containing compound and at least one tin- or germanium-containing promoter.

16 Claims, No Drawings

PROCESS FOR PREPARING PROPYLENE GLYCOL MONOALKYL ETHERS AND ALKOXYACETONES

BACKGROUND OF THE INVENTION

1. Field of the Invention

This invention relates to a process for the preparation of propylene glycol monoalkyl ethers and alkoxyacetones by the reaction of synthesis gas, i.e., a mixture of hydrogen and carbon monoxide with (a) acetaldehyde or (b) an acetal and an alcohol utilizing as a catalyst a cobalt-containing compound and a promoter.

2. Prior Art

There is a ever increasing need for a wide variety of glycol monoalkyl ethers of different carbon numbers and structures which have become important present articles of commerce. Such ethers are employed in a wide variety of applications as solvents, reaction media, etc. In conventional processes an olefin oxide such as ethylene oxide and propylene oxide is first prepared from an olefin and reacted with suitable alcohol. Since the cost of materials derived from petroleum sources has been rising rapidly, research efforts are now being made to find a new process for producing these glycol ethers which does not utilize an olefin as a starting material. One of the newer methods for the preparation of glycol monoalkylethers, in which an acetal is reacted with carbon monoxide and hydrogen in the presence of a cobalt carbonyl catalyst, is described in German Pat. Nos. 875,802 and 890,945. This process suffers from several disadvantages including a low selectivity of the glycol ether and decomposition of the carbonyl catalyst during recovery of the product from the reaction mixture.

In the U.S. Pat. No. 4,071,568 a process for making glycol monoalkyl ethers is disclosed in which the catalyst utilized is cobalt carbonyl combined with a trivalent organic phosphorus compound such as tri-n-butylphosphine which is reported to give better selectivity. Other processes for preparing glycol monoalkyl ethers are described in U.S. Pat. No. 4,062,898 and in German Pat. No. 2,741,589.

One of the objects of this invention is to provide a novel process for preparing propylene glycol monoalkyl ethers and alkoxyacetones by means of a unique catalyst system in which the feedstock utilized comprises acetaldehyde or acetal, an alcohol and synthesis gas.

Another object of this invention is to provide a process for producing propylene glycol monoalkyl ethers and alkoxyacetones in high yield.

SUMMARY OF THE INVENTION

In this invention propylene glycol monoalkyl ethers and alkoxyacetones are prepared by contacting a mixture of carbon monoxide, hydrogen, acetaldehyde or an acetal and a monohydric alcohol with a catalyst comprising a cobalt-containing compound and a promoter which is a tin-or germanium-containing compound at superatmospheric pressures of about 500 psig or greater and at a temperature of from about 50° to about 350° C.

The process of this invention is set out in the following equation where for purposes of illustration the reaction of carbon monoxide, hydrogen, acetaldehyde and an alcohol is shown:

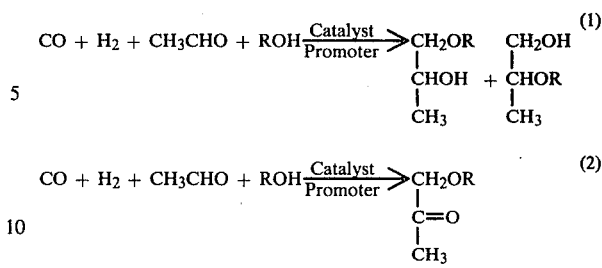

Under certain operating conditions, alkoxyacetones are formed as the major products in this process according to the reaction scheme of equation (2) above.

A high degree of selectivity is exhibited by the reaction of the process of this invention. For example, when acetaldehyde and ethanol are reacted with synthesis gas substantial yields of the propylene glycol monoethyl ethers and the ethoxyacetone are obtained.

DETAILED DESCRIPTION OF THE INVENTION

This invention relates to a process for preparing propylene glycol monoalkyl ethers and alkoxyacetones by a process which comprises reacting a mixture of hydrogen and carbon monoxide and (a) acetaldehyde or (b) an acetal and an alcohol of the formula:

ROH, wherein R is an alkyl radical of from 1 to 10 carbon atoms, in the presence of a catalyst comprising a cobalt-containing compound and at least one promoter selected from the group consisting of a tin- or a germanium-containing compound at superatmospheric pressures of about 500 psi or greater and at a temperature of about 50° to about 350° C.

In carrying out the reaction of this invention selectively to produce high yields of the desired propylene glycol monoalkylethers and/or alkoxyacetones it is necessary to supply sufficient carbon monoxide, hydrogen, aldehyde or acetal and alcohol to at least satisfy the stoichiometry of equations (1) and/or (2) above although an excess of one or more of the reactants over the stoichiometric amounts may be present.

Catalysts that are suitable for use in the practice of this invention contain cobalt. The cobalt-containing compounds may be chosen from a wide variety of organic or inorganic compounds, complexes, etc., as will be shown and illustrated below. It is only necessary that the catalyst precursor actually employed contain said metal in any of its ionic states. The actual catalytically active species is then believed to comprise cobalt in complex combination with one or more ligands and with carbon monoxide and hydrogen. The most effective catalyst is achieved where the cobalt hydrocarbonyl species is solubilized in the alcohol coreactant employed.

The cobalt-containing catalyst precursors may take many different forms. For instance, the cobalt may be added to the reaction mixture in an oxide form, as in the case of, for example, cobalt(II) oxide (CoO) or cobalt-(II, III) oxide ($Co_3O_4$). Alternatively, it may be added as the salt of a mineral acid, as in the case of cobalt(II) chloride ($CoCl_2$), cobalt(II) chloride hydrate ($CoCl_2.6H_2O$), cobalt(II) bromide ($CoBr_2$), cobalt(II) iodide ($CoI_2$) and cobalt(II) nitrate hydrate ($Co(NO_3)_2.6H_2O$), etc., or as the salt of a suitable organic carboxylic acid, for example, cobalt(II) formate, cobalt(II) acetate, cobalt(II) propionate, cobalt naphthenate, cobalt acetylacetonate, etc. The cobalt may also be added to the reaction zone as a carbonyl or hydrocarbonyl derivative. Here, suitable examples include dicobalt octacarbonyl ($Co_2(CO)_8$), cobalt hydrocarbonyl ($HCo(CO)_4$) and substituted carbonyl species such as the triphenylphosphine cobalt tricarbonyl dimer, etc.

Preferred cobalt-containing compounds include oxides of cobalt, cobalt salts of a mineral acid, cobalt salts of organic carboxylic acids and cobalt carbonyl or hydrocarbonyl derivatives. Among these, particularly preferred are cobalt(II) chloride, cobalt acetylacetonate, cobalt(II) acetate, cobalt(II) propionate, and dicobalt octacarbonyl.

As previously pointed out in the process of this invention the reaction is conducted in the presence of a catalyst comprising a cobalt-containing compound and a tin- or germanium-containing promoter. The cobalt-containing compound employed may be a cobalt carbonyl or a compound capable of forming a cobalt carbonyl under reaction conditions.

The tin-containing promoter compounds which may be utilized with the cobalt-containing compounds in this process may also take many different forms. For instance the tin may be added to the reaction mixture in elemental form, or in the form of a halide, such as stannic chloride, stannous iodide, stannic bromide, or a hydrocarbyl tin compound such as tetraphenyltin, tetra-n-butyltin, hexamethylditin, tetramethyltin, and dibutyl diphenyltin, or as organo-halide tin compound such as trimethyltin chloride, di-t-butyltin dichloride, dimethyltin dichloride, methyltin trichloride, phenyltin trichloride, triethyltin bromide, trimethyltin bromide and tributyltin bromide, or an organotin hydride such as tributyltin hydride, or an organotin oxide such as dimethyltin oxide and diphenyltin oxide, or a carboxylate such as tin(II) caproate, tributyltin acetate, and tri-n-propyltin acetate, or an oxide such as stannous oxide and stannic oxide.

The preferred tin-containing promoter compounds are the organo-halide tin compounds. Among these, particularly preferred are trimethyltin chloride, tributyltin hydride and tributyltin bromide.

The germanium-containing promoter compounds which may be utilized with the cobalt-containing compounds in this process may also take many different forms. For instance, the germanium may be added to the reaction mixture in the form of a halide, such as germanium tetrachloride, germanium diiodide and germanium tetrabromide, or as a hydrocarbyl-germanium compound such as tetra-n-butylgermane, tetraethylgermane, tetraphenylgermane and tetramethylgermane, or as organo-halide germanium compound such as diphenylgermanium chloride, methylgermanium trichloride, phenylgermanium trichloride, tri-n-butylgermanium iodide, triethylgermanium chloride, triethylgermanium iodide, trimethylgermanium chloride, triphenylgermanium bromide and triphenylgermanium chloride or an organo-germanium hydride, such as triphenylgermanium hydride, or an organogermanium oxide or carboxylate such as triphenylgermanium acetate, or a germanium alkoxide such as germanium butoxide, germanium ethoxide and germanium methoxide.

The preferred germanium-containing promoter compounds are the organo-halide germanium compounds, the hydrocarbylgermanium compounds and the organogermanium hydrides. Amoung these, particularly preferred are triphenylgermanium bromide, triphenylgermanium hydride, trimethylgermanium chloride, triphenylgermanium chloride, trimethylgermanium bromide, triethylgermanium chloride, tetraphenylgermane and tetramethylgermane.

The number of gram moles of the tin-containing or germanium-containing compound employed per gram atom of cobalt can be varied widely in this process and is generally in the range of 0.01 to 100 and preferably from 0.1 to 5.

The quantity of cobalt catalyst employed in the instant invention is not critical and may vary over a wide range. In general, the novel process is desirably conducted in the presence of a catalytically effective quantity of one or more of the active cobalt species together with one or more of the tin- or germanium-containing promoters which gives the desired products in reasonable yields. The reaction proceeds when employing as little as about $1 \times 10^{-6}$ weight percent and even lesser amount of cobalt, basis the total weight of the reaction mixture. The upper concentration is dictated by a variety of factors including catalyst cost, partial pressures of carbon monoxide and hydrogen, operating temperature, etc. A cobalt catalyst concentration of from about $1 \times 10^{-5}$ to about 10 weight percent cobalt, based on the total weight of reaction mixture, is generally desirable in the practice of this invention.

Alcohols useful as starting materials in the process of this invention (see eq. 1 and 2 above) have the formula:

ROH where R is an alkyl radical of from 1 to 10 carbon atoms. Suitable alcohols include methanol, ethanol, propanol, butanol, heptanol, decanol, etc. and isomers thereof.

Acetals which may be utilized in the process of this invention include compounds of the formula:

$(R'O)_2CH_2CH_3$ where R' is an alkyl radical of from 1 to 10 carbon atoms as exemplified by methyl, ethyl, butyl, hexyl, nonyl etc. and isomers thereof. The preferred acetals include 1,1-dimethoxyethane, 1,1-diethoxyethane (commonly known as acetal) and 1,1-di-n-propyloxyethane. Where the acetal or acetaldehyde are used in combination with an alcohol, as defined supra, the ratio of alcohol to aldehyde is not critical but is usually in the range of 0.01 to 100 moles of alcohol per mole of aldehyde.

The relative amounts of carbon monoxide and hydrogen which may be initially present in the syngas mixture are also variable, and these amounts may be varied over a wide range. In general, the mole ratio of $CO:H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether.

The temperature range which can usefully be employed in these syntheses is a further variable, dependent upon other experimental factors, including the choice of the alcohol, the pressure, and the concentration and choice of particular species of the cobalt-containing compound and the promoter compounds among other things. The range of operability is from about 50° to about 350° C. when super-atmospheric pressures of syngas are employed. A narrower range of about 100° to about 250° C. represents the preferred temperature range.

Superatmospheric pressure of about 500 psi or greater leads to substantial yields of desirable glycol ethers by the process of this invention. A preferred operating range is from about 1000 psi to about 10,000 psi, although pressures above 10,000 psi also provide useful yields of the desired products. The pressures referred to here represent the total preessure generated by all the reactants, although they are substantially due to the carbon monoxide and hydrogen fractions in these examples.

As far as can be determined, without limiting the invention thereby, the one-step process disclosed herein leads primarily to the utilizing the disclosed catalysts for the formation of propylene glycol monoalkyl ethers and alkoxyacetone products. The propylene monoalkyl ethers may be generated in this process in two isomeric forms, i.e., the propylene glycol α-monoalkyl ethers and propylene glycol β-monoalkyl ethers which have the general structures I and II respectively, where in this case R is an alkyl radical of from 1 to 10 carbon atoms.

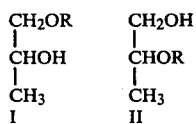

In the case where acetaldehyde and ethanol are the coreactants, the principal products are the propylene glycol monoethyl ethers and ethoxyacetone. By-products such as water, ethanol and diethyl ether are also detected in the liquid product fraction.

The novel process of this invention can be conducted in a batch, semicontinuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired ether products, and said material may be recovered by methods well know in the art, such as distillation, fractionation, extraction and the like. A fraction rich in the cobalt-containing compound and the promoter compound may then be recycled to the reaction zone, if desired, and additional products generated.

The products formed by the process of this invention have been identified in this work by one or more of the following analytical procedure, viz, gas-liquid phase chromatograph (glc), infrared (ir), mass spectrometry, nuclear magnetic resonance (nmr) and elemental analysis, or a combination of these techniques. Analysis have, for the most part, been by parts in weight; all temperatures are in degrees centigrade and all pressures in pounds per square inch gauge (psig).

The following examples which illustrate various embodiments of the invention are to be considered not limitative.

EXAMPLE 1

A 450 ml glass-lined pressure reactor was charged with a mixture of dicobalt octacarbonyl (20 mmole Co), triphenylgermanium hydride (2.0 mmole) and 1,1-diethoxyethane i.e., acetal (0.1 mole) in 23.0 g of ethanol (0.5 mole). The mixture was charged under a nitrogen atmosphere, the reactor sealed, flushed with $CO/H_2$ (1:2 molar), pressured to 4500 psig with 1:2 molar syngas ($CO/H_2$) and then heated to 180° C. with agitation.

After carbonylation the reactor was cooled, the gas pressure noted (4015 psig), the excess gas sampled and vented, and the dark brown liquid product (40.5 g) recovered.

Analysis of the liquid product by glc and Karl Fischer titration showed it to contain:
4.9% propylene glycol α-monoethyl ether
3.0% propylene glycol β-monoethyl ether
0.7% 1-ethoxyacetone
4.5% water
7.8% diethylether
66.6% ethanol
1.4% unreacted acetal Estimated yield of propylene glycol monoethyl ethers (Basis acetal charged)
= 31 mole %.

Yield of propylene glycol monoethyl ethers + 1-ethoxyacetone (basis acetal converted)
= 35 mole %.

Typical off-gas samples showed the presence of:
66% hydrogen
27% carbon monoxide
3.4% carbon dioxide The propylene glycol monoethyl ethers were recovered from the crude liquid product by fractional distillation in vacuo.

EXAMPLE 2

Following the operating procedures of Example 1, the reactor was charged with a mixture of dicobalt octacarbonyl (2 mmole Co), triethylgermanium chloride (2.0 mmole Co), acetal (0.05 mole) and 13.80 g. of ethanol (0.3 mole). After pressuring to 4500 psig with 1:2 molar syngas ($CO/H_2$), the reactor was heated to 180° C. with agitation.

After 8 hours, the reactor was cooled, the gas pressure noted (3700 psig), the excess gas sampled and vented and the red liquid product (22.3 g) recovered.

Analysis of the liquid product by glc and Karl Fischer titration showed it to contain:
6.2% propylene glycol α-monoethyl ether
4.0% propylene glycol β-monoethyl ether
0.2% ethoxyacetone
4.9% water
1.5% diethyl ether
69.8% ethanol
0.2% unreacted acetal Estimated yield of propylene glycol monoethyl ethers (basis acetal charged)
= 44 mole %

-continued
Yield of propylene glycol monoethylethers +
ethoxyacetone (basis acetal converted)
= 45 mole %

Typical off-gas samples showed the presence of:
55% hydrogen
40% carbon monoxide
37% carbon dioxide Analysis of the liquid product by atomic absorption showed it to contain 98% of the cobalt originally charged. There was no solid product phase.

EXAMPLE 3

Following the operating procedures of Example 1, the reactor was charged with a mixture of dicobalt octacarbonyl (2 mmole Co), triphenylgermanium hydride (2.0 mmole), acetaldehyde (0.1 mole) and 37.1 g of n-butanol (0.5 mole). After pressurizing to 2700 psig with 1:2 molar syngas ($CO/H_2$), the reactor was heated to 160° C. with agitation.

After four hours, the reactor was cooled, the gas pressure (2565 psig) noted, the excess gas sampled and vented and the deep-red liquid product (44.2 g) recovered. There was no solid phase.

Analysis of the liquid product by glc and Karl Fischer titration showed it to contain:
6.6% n-butoxypropanone
3.1% propylene glycol monobutyl ethers
5.3% water
79.3% n-butanol
0.2% unreacted acetaldehyde Typical off-gas samples show the presence of:
56.5% hydrogen
31.6% carbon monoxide
2.2% carbon dioxide

EXAMPLE 4

Following the operating procedures of Example 1, the reactor was charged with a mixture of dicobalt octacarbonyl (2 mmole Co), triphenylgermanium hydride (2.0 mmole), acetaldehyde (0.1 mole) and 18.0 g of n-propanol (0.3 mole). After pressuring to 4500 psi with 2:1 molar syngas ($CO/H_2$), the reactor was heated to 180° C. with agitation.

After four hours, the reactor was cooled, the gas pressure noted (3950 psig) the excess gas sampled and vented and the liquid product (24.9 g) recovered.

Analysis of the liquid product by glc and Karl Fischer titration showed it to contain:
4.8% propylene glycol monopropyl ethers
4.2% n-propoxyacetone
4.5% water
66.9% n-propanol
7.7% ethanol
0.5% unreacted acetaldehyde Typical off-gas samples showed the presence of:
2.9% hydrogen
7.0% carbon monoxide
0.1% carbon dioxide Analysis of the liquid product showed it to contain >98% of the cobalt originally charged. There was no solid product phase.

EXAMPLE 5

Following the operating procedure of Example 3, the reactor was charged with a mixture of dicobalt octacarbonyl (2 mmole Co), triphenylgermanium hydride (2.0 mmole), acetaldehyde (0.1 mole) and 37.1 g of n-butanol. After pressuring to 4500 psig with 1:2 molar syngas ($CO/H_2$) the reactor was heated to 180° C. with agitation.

After four hours, the reactor was cooled, the gas pressure noted (4150 psig), the excess gas sampled and vented and the liquid product (44.1 g) recovered.

Analysis of the liquid product by glc and Karl Fischer titration showed it to contain:
5.6% propylene glycol monobutyl ethers
1.8% n-butoxypropanone
2.8% water
76.9% n-butanol
5.2% ethanol
<0.1% unreacted acetaldehyde Typical off-gas samples showed the presence of:
5.6% hydrogen
4.1% carbon monoxide
2.0% carbon dioxide Analysis of the liquid product showed it to contain >98% of the cobalt originally charged. There was no solid process phase.

EXAMPLE 6-19

Using the same procedure as in Example 1, a number of additional examples were carried out in which acetal was reacted with carbon monoxide and hydrogen in the presence of a variety of tin and germanium promoters. Data relating to these examples are included in Tables I and II which follow.

It may be noted that:

(1) Propylene glycol monoethyl ethers may be generated from synthesis gas, acetal (1,1-diethoxyethane) and ethanol using solubilized cobalt octacarbonyl coupled with a variety of tin and germanium promoters. Suitable promoters include triphenylgermanium bromide, triphenylgermanium hydride, triethylgermanium chloride, tetraethylgermane, trimethylgermanium bromide and tetraphenylgermane.

(2) Cobalt recovery in solution was >98% for many of these cobalt catalyst combinations.

(3) Syntheses were conducted over the temperature range 160°–180° C. when employing reaction times of 4 to 18 hours.

TABLE I

| | Propylene Glycol Monoalkyl Ethers By Reaction of Synthesis Gas, Ethanol and Acetal[a] | | | | | | | | | |
|---|---|---|---|---|---|---|---|---|---|---|
| | Catalyst | Aldehyde | Time | Liquid Product Composition (Wt. %)[b] | | | | | | Cobalt |
| Example | Composition | Coreactant | Hour | 1-Et, 2-Pro | 2-Et, 1-Pro | 1-EtAcet | Acetal | $H_2O$ | EtOH | Recovered (%) |
| 6 | $Co_2(CO)_8$—$Ph_3GeBr$ | Acetal | 4 | 1.4 | 1.5 | 8.8 | 1.4 | 2.6 | 70.0 | >98 |
| 7 | $Co_2(CO)_8$—$Ph_3GeH$ | Acetal | 4 | 1.0 | 1.6 | 8.6 | 1.5 | 3.0 | 73.5 | |
| 8 | $Co_2(CO)_8$—$Me_3GeBr$ | Acetal | 4 | 1.7 | 1.6 | 8.4 | 0.7 | 3.5 | 70.6 | >98 |
| 9 | $Co_2(CO)_8$—$Bu_3SnH$ | Acetal | 4 | 0.1 | | 6.7 | 17.6 | 1.4 | 64.6 | >98 |
| 10 | $Co_2(CO)_8$—$Bu_3SnCl$ | Acetal | 4 | 0.6 | | 7.5 | 3.0 | 2.1 | 78.2 | |

TABLE I-continued

Propylene Glycol Monoalkyl Ethers By Reaction of Synthesis Gas, Ethanol and Acetal[a]

| Example | Catalyst Composition | Aldehyde Coreactant | Time Hour | Liquid Product Composition (Wt. %)[b] | | | | | | Cobalt Recovered (%) |
|---|---|---|---|---|---|---|---|---|---|---|
| | | | | 1-Et, 2-Pro | 2-Et, 1-Pro | 1-EtAcet | Acetal | $H_2O$ | EtOH | |
| 11 | $Co_2(CO)_8$—$Et_4Ge^c$ | Acetal | 4 | 5.8 | 5.0 | 4.2 | 2.6 | 4.2 | 65.2 | |
| 12 | $Co_2(CO)_8$—$Ph_4Ge^c$ | Acetal | 4 | 4.2 | 3.5 | 4.1 | 2.2 | 3.3 | 73.3 | |
| 13 | $Co_2(CO)_8$—$Et_3GeCl^c$ | Acetal | 4 | 4.7 | 4.8 | 5.7 | 2.2 | 3.6 | 66.4 | >98 |

[a]Run Conditions: Co, 2 mmole; Ge/Sn, 2 mmole; Acetal, 0.1 mole; EtOH, 0.3 mole; 160° C.; 2700 psig ($CO/H_2$, 1:2 Molar).
[b]Abbrev: 1-Et, 2-Pro, $CH_2OEt$; 2-Et, 1-Pro, $CH_2OH$; 1-EtAcet, $CH_2OEt$
$\phantom{xxxxxxxx}$ | $\phantom{xxxxxxxx}$ | $\phantom{xxxxxxxx}$ |
CHOH $\phantom{xxxx}$ CHOEt $\phantom{xxxx}$ C=O
| $\phantom{xxxxxxxx}$ | $\phantom{xxxxxxxx}$ | $\phantom{xxxxxxxx}$ |
$CH_3\phantom{xxxx}$ $CH_3\phantom{xxxx}$ $CH_3$

[c]Run Conditions: 180° C., 4500 psig ($CO/H_2$, 1:2 molar).

TABLE II

Propylene Glycol Monoalkyl Ethers from Synthesis Gas, Ethanol and Acetal[a]

| Example | Catalyst Composition | Aldehyde Coreactant | Time Hour | Liquid Product Composition (Wt. %)[b] | | | | | | | Cobalt Recovered (%) |
|---|---|---|---|---|---|---|---|---|---|---|---|
| | | | | 1-Et, 2-Pro | 2-Et, 1-Pro | 1-EtAcet | Acetal | $H_2O$ | EtOH | $Et_2O$ | |
| 14 | $Co_2(CO)_8$—$Et_3GeCl$ | Acetal[d] | 8 | 6.2 | 4.0 | 0.2 | 0.2 | 4.9 | 69.8 | 1.5 | >98 |
| 15 | $Co_2(CO)_8$—$Ph_3GeH^c$ | Acetal | 18 | 5.8 | 4.9 | Trace | 1.5 | 2.6 | 54.7 | 9.0 | |
| 16 | $Co_2(CO)_8$—$Ph_3GeH^c$ | Acetal[d] | 8 | 4.2 | 4.0 | 0.2 | 2.8 | 5.0 | 72.6 | 5.9 | |
| 17 | $Co_2(CO)_8$—$Ph_3GeBr^c$ | Acetal[d] | 8 | 5.6 | 3.1 | 0.2 | 2.3 | 5.0 | 68.4 | 5.8 | |
| 18 | $Co(OAc)_2$—$Ph_3GeBr^c$ | Acetal[d] | 8 | 3.9 | 3.3 | 0.2 | 2.5 | 4.0 | 69.6 | 6.9 | |
| 19 | $Co_2(CO)_8$—$Ph_3GeBr$ | Acetal[d,e] | 4 | 0.4 | | 7.1 | 6.2 | 2.7 | 77.5 | 1.6 | >98 |

[a]Run conditions: Co, 2 mmole; Ge/Sn, 2 mmole; Acetal, 0.1 mole; EtOH, 0.3 mole; 160° C., 2700 psig ($CO/H_2$, 1:2 molar)
[b]Abbrev. 1-Et, 2-Pro, $CH_2OEt$; 2-Et, 1-Pro, $CH_2OH$; 1-EtAcet = $CH_2OEt$
$\phantom{xxxxxxxx}$ | $\phantom{xxxxxxxx}$ | $\phantom{xxxxxxxx}$ |
CHOH $\phantom{xxxx}$ CHOEt $\phantom{xxxx}$ C=O
| $\phantom{xxxxxxxx}$ | $\phantom{xxxxxxxx}$ | $\phantom{xxxxxxxx}$ |
$CH_3\phantom{xxxx}$ $CH_3\phantom{xxxx}$ $CH_3$

[c]Run conditions: 180° C., 4500 psig ($CO/H_2$, 1:2 molar)
[d]0.05 mole, Acetal
[e]3000 psig $CO/H_2$, 2:1 molar

EXAMPLE 20

A 450 ml glass-lined pressure reactor was charged with a mixture of dicobalt octacarbonyl (2.0 mmole Co) and tetraethylgermane (2.0 mmole) in 1,1-dimethoxyethane (0.1 mole, 9.01 g) and methanol (0.3 mole, 9.60 g). The mixture was charged under a nitrogen atmosphere, the reactor sealed, flushed with $CO/H_2$ (1:1 molar), pressured to 2700 psig with 1:1 molar syngas ($H_2/CO$) and then heated to 130° C. with agitation.

After 4 hours at temperature the reactor was cooled, the gas pressure noted (2500 psig), the excess gas sampled and vented, and the red liquid product (19.6 g, 23 ml) recovered. There was no solid precipitate at this stage.

Analysis of the liquid product by glc and Karl Fischer titration shows it to contain:
9.0% methoxyacetone
3.9% water
0.8% propylene glycol monomethyl ether
24.3% unreacted 1,1-dimethoxyethane
5.8% unreacted acetaldehyde
46.1% unreacted methanol
0.1% ethanol Estimated conversion of 1,1-dimethoxyethane+acetaldehyde=24%. Estimated yield of methoxyacetone (basis aldehyde+acetal converted)=82%. Cobalt recovery in the product solution was >98%.

Analysis of a typical gas sample showed the presence of:
58% carbon monoxide
41% hydrogen
0.2% carbon dioxide The methoxyacetone was recovered from the crude liquid product by fractional distillation in vacuo. Identification of the product fractions was confirmed by glc trapping and nmr analyses.

EXAMPLES 20-32

Following the same procedure as in Example 20 a number of additional examples were carried out in which 1,1-dimethoxyethane and methanol were reacted with synthesis gas in the presence of a variety of germanium and tin promoters. Data relating to these examples are included in Tables III and IV which follow.

TABLE III

Methoxyacetone From Synthesis Gas Plus 1,1-Dimethoxyethane[a]

| Example | Catalyst Composition | Liquid Product Composition (%)[b] | | | | | | | Acetal Conv (%) | MeAcet[c] Yield (%) | Cobalt Recov. (%) |
|---|---|---|---|---|---|---|---|---|---|---|---|
| | | MeAcet | 2-Me-1-Pro + 1-Me-2-Pro | Acetal | $CH_3CHO$ | MeOH | $H_2O$ | EtOH | | | |
| 20 | $Co_2(CO)_8$—$Et_4Ge$ | 9.0 | 0.8 | 24.3 | 5.8 | 46.1 | 3.9 | 0.1 | 24 | 82 | >98 |
| 21 | $Co_2(CO)_8$—$Ph_3GeCl$ | 6.4 | 0.2 | 29.1 | 6.0 | 47.0 | 3.6 | 0.1 | 17 | 78 | >98 |
| 22 | $Co_2(CO)_8$—$Ph_3GeBr$ | 4.7 | 0.2 | 30.6 | 6.7 | 46.3 | 4.5 | 0.1 | 10 | >95 | 27 |
| 23 | $Co_2(CO)_8$—$CsGeCl_3$ | 1.1 | 0.2 | 28.8 | 3.2 | 57.5 | 1.9 | — | 22 | 11 | >98 |
| 24 | $Co_2(CO)_8$—$Ph_4Ge$ | 7.2 | 0.2 | 24.4 | 4.7 | 46.7 | 4.4 | 0.3 | 24 | 70 | >98 |
| 25 | $Co_2(CO)_8$—$Me_3GeI$ | 2.4 | 0.2 | 32.3 | 17.7 | 20.3 | 12.6 | 0.5 | <10 | N.D.[d] | >98 |

TABLE III-continued

Methoxyacetone From Synthesis Gas Plus 1,1-Dimethoxyethane[a]

| Example | Catalyst Composition | Liquid Product Composition (%)[b] | | | | | | | Acetal Conv (%) | MeAcet[c] Yield (%) | Cobalt Recov. (%) |
|---|---|---|---|---|---|---|---|---|---|---|---|
| | | MeAcet | 2-Me-1-Pro + 1-Me-2-Pro | Acetal | CH$_3$CHO | MeOH | H$_2$O | EtOH | | | |
| 26 | Co$_2$(CO)$_8$—Me$_3$GeBr | 5.0 | 0.2 | 31.2 | 4.5 | 40.3 | 4.6 | 0.1 | 11.8 | >95 | >98 |
| 27 | Co$_2$(CO)$_8$—Et$_3$GeCl | 7.2 | 0.3 | 27.7 | 5.4 | 45.2 | 3.9 | 0.3 | 17 | 93 | >98 |
| 28 | Co$_2$(CO)$_8$—Bu$_3$SnH | 1.3 | 0.1 | 34.6 | 2.9 | 48.2 | 1.2 | 1.2 | 20 | 13 | >98 |

[a]Reaction charge: Co$_2$(CO)$_8$, 2.0 mmole Co; Ge/Sn, 2.0 mmole; MeOH, 0.3 mole; 1,1-dimethoxyethane, 0.1 mole.
Reaction conditions: 130° C., 2700 psig CO/H$_2$ (1:1) initial pressure, 4 hours
[b]Abbreviations: MeAcet, MeOCH$_2$CCH$_3$; 1-Me-2-Pro, MeOCH$_2$CHCH$_3$; 2-Me-1-Pro, HOCH$_2$CHCH$_3$; Acetal, (MeO)$_2$CHCH$_3$.
$\quad\quad\quad\quad\quad\quad\quad\quad\quad\quad$ ‖ $\quad\quad\quad\quad\quad\quad$ | $\quad\quad\quad\quad\quad\quad$ |
$\quad\quad\quad\quad\quad\quad\quad\quad\quad\quad$ O $\quad\quad\quad\quad\quad\quad$ OH $\quad\quad\quad\quad\quad\quad$ OMe
[c]Methoxyacetone yield basis acetaldehyde + acetal converted
[d]N.D., Not Determined

TABLE IV

Methoxyacetone From Synthesis Gas Plus 1,1-Dimethoxyethane[a]

| Example | Catalyst Composition | Operating Temp. (°C.) | Liquid Product Composition (%)[b] | | | | | | Acetal Conv (%) | MeAcet[c] Yield (%) |
|---|---|---|---|---|---|---|---|---|---|---|
| | | | MeAcet | 2-Me-1-Pro + 1-Me-2-Pro | Acetal | CH$_3$CHO | MeOH | EtOH | | |
| 29 | Co$_2$(CO)$_8$—Et$_3$GeCl | 130 | 7.2 | 0.3 | 27.7 | 5.4 | 45.2 | 0.3 | 17 | 93 |
| 30 | Co$_2$(CO)$_8$—Et$_3$GeCl | 145 | 7.9 | 0.4 | 19.1 | 5.5 | 46.6 | 1.0 | 30 | 62 |
| 31 | Co$_2$(CO)$_8$—Et$_3$GeCl | 160 | 8.3 | 0.7 | 10.1 | 5.1 | 46.7 | 4.6 | 48 | 45 |
| 32 | Co$_2$(CO)$_8$—Et$_3$GeCl | 180 | 4.1 | 6.0 | 4.6 | 3.8 | 39.3 | 8.2 | 69 | 15 |

[a]Reaction charge: Co$_2$(CO)$_8$, 2.0 mmole Co; Ge, 2.0 mmole; MeOH, 0.3 mole; 1,1-dimethoxyethane, 0.1 mole.
Reaction conditions: 2700 psig CO/H$_2$ (1:1) initial pressure, 4 hours
[b]Abbreviations: MeAcet, MeOCH$_2$CCH$_3$; 1-Me-2-Pro, MeOCH$_2$CHCH$_3$; 2-Me-1-Pro, HO—CH$_2$CHCH$_3$; Acetal (MeO)$_2$CHCH$_3$.
$\quad\quad\quad\quad\quad\quad\quad\quad\quad\quad$ ‖ $\quad\quad\quad\quad\quad\quad$ | $\quad\quad\quad\quad\quad\quad$ |
$\quad\quad\quad\quad\quad\quad\quad\quad\quad\quad$ O $\quad\quad\quad\quad\quad\quad$ OH $\quad\quad\quad\quad\quad\quad$ OMe
[c]Methoxyacetone yield basis acetaldehyde + acetal converted

What is claimed is:

1. A process for preparing propylene glycol monoalkyl ethers and alkoxyacetones which comprises reacting a mixture of hydrogen, carbon monoxide, a material selected from the group consisting of (a) acetaldehyde and (b) an acetal of the formula:

(R'O)$_2$CHCH$_3$ wherein R' is an alkyl radical of from 1 to 10 carborn atoms, and an alcohol of the formula:

ROH, wherein R is an alkyl radical of from 1 to 10 carbon atoms, in the presence of a catalyst comprising a cobalt-containing compound and a promoter selected from the group consisting of tin- and germanium-containing compounds at superatmospheric pressures of about 500 psi or greater and at a temperature of from about 50° to about 350° C.

2. The process of claim 1 wherein the said reaction mixture is heated at a temperature of about 100° to about 250° C.

3. The process of claim 1 wherein the process is conducted at a pressure of about 1000 psi to about 10,000 psig.

4. The process of claim 1 wherein the said cobalt-containing compound is selected from the group consisting of one or more oxides of cobalt, cobalt salts of a mineral acid, cobalt salts of an organic carboxylic acid and cobalt carbonyl or hydrocarbonyl derivatives.

5. The process of claim 1 wherein the said cobalt-containing compound is selected from the group consisting of cobalt oxide, cobalt chloride, cobalt iodide, cobalt nitrate, cobalt sulfate, cobalt acetate, cobalt propionate, cobalt acetylacetonate, and dicobalt octacarbonyl.

6. The process of claim 1 wherein said cobalt-containing compound is dicobalt octacarbonyl.

7. The process of claim 1 wherein the said promoter is a tin-containing compound.

8. The process of claim 7 wherein the said tin-containing compound is selected from the group consisting of tributyltin hydride and tributyltin bromide.

9. The process of claim 1 wherein the said promoter is a germanium-containing compound.

10. The process of claim 9 wherein the said germanium-containing compound is selected from the group consisting of triphenylgermanium bromide, triphenylgermanium hydride, triethylgermanium chloride, tetraethylgermane, tetraphenylgermane and trimethylgermanium bromide.

11. The process of claim 1 wherein the said material is acetaldehyde.

12. The process of claim 1 wherein said material is an acetal and an alcohol.

13. The process of claim 12 wherein the said acetal is 1,1-diethoxyethane.

14. The process of claim 12 wherein the said alcohol is selected from the group consisting of methanol, ethanol, propanol, butanol, pentanol and isomers thereof.

15. The process of claim 12 wherein the said alcohol is ethanol.

16. The process of claim 12 wherein the said alcohol is n-butanol.

* * * * *